United States Patent
Ni et al.

(10) Patent No.: US 7,720,535 B2
(45) Date of Patent: May 18, 2010

(54) PACING MANAGEMENT DURING CARDIOPULMONARY RESUSCITATION

(75) Inventors: Quan Ni, Shoreview, MN (US); Yanting Dong, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 702 days.

(21) Appl. No.: 11/209,975

(22) Filed: Aug. 23, 2005

(65) Prior Publication Data
US 2007/0049976 A1    Mar. 1, 2007

(51) Int. Cl.
*A61N 1/36* (2006.01)
*A61N 1/39* (2006.01)

(52) U.S. Cl. .................. 607/3; 607/4; 607/17; 600/515

(58) Field of Classification Search .............. 607/3; 600/515
See application file for complete search history.

(56) References Cited

U.S. PATENT DOCUMENTS

| | | | |
|---|---|---|---|
| 4,904,472 A | 2/1990 | Belardinelli et al. | |
| 4,980,379 A | 12/1990 | Belardinelli et al. | |
| H1347 H | 8/1994 | Greeninger et al. | |
| 5,549,652 A | 8/1996 | McClure et al. | |
| 6,247,474 B1 | 6/2001 | Greeninger et al. | |
| 6,263,246 B1 | 7/2001 | Goedeke et al. | |
| 6,334,070 B1* | 12/2001 | Nova et al. | 607/5 |
| 6,381,492 B1 | 4/2002 | Rockwell et al. | |
| 6,409,675 B1 | 6/2002 | Turcott | |
| 6,415,174 B1 | 7/2002 | Bebehani et al. | |
| 6,463,327 B1* | 10/2002 | Lurie et al. | 607/42 |
| 6,480,733 B1 | 11/2002 | Turcott | |
| 6,491,639 B1 | 12/2002 | Turcott | |
| 6,644,322 B2 | 11/2003 | Webb | |
| 6,650,940 B1 | 11/2003 | Zhu et al. | |
| 6,662,050 B2 | 12/2003 | Olson | |
| 6,754,538 B2 | 6/2004 | Linberg | |
| 6,766,198 B1 | 7/2004 | Snell | |
| 6,804,558 B2 | 10/2004 | Haller et al. | |
| 7,226,427 B2* | 6/2007 | Steen | 601/44 |
| 2003/0060723 A1 | 3/2003 | Joo et al. | |
| 2003/0088278 A1 | 5/2003 | Bardy et al. | |
| 2004/0039420 A1* | 2/2004 | Jayne et al. | 607/5 |
| 2004/0162510 A1* | 8/2004 | Jayne et al. | 601/41 |
| 2008/0071316 A1* | 3/2008 | Freeman | 607/5 |

* cited by examiner

*Primary Examiner*—Carl H Layno
*Assistant Examiner*—Natasha N Patel
(74) *Attorney, Agent, or Firm*—Hollingsworth & Funk, LLC

(57) ABSTRACT

Systems and methods provide for coordinated cardiac pacing with delivery of cardiopulmonary resuscitation (CPR) to a patient. Managing cardiac pacing in a patient during a cardiac arrhythmia involves detecting a cardiac arrhythmia using a patient implantable medical device, prompting a cardiopulmonary resuscitation compression, and delivering, using the patient implantable medical device, a pacing pulse to a heart chamber in coordination with the compression prompt.

19 Claims, 5 Drawing Sheets

PACING MANAGEMENT DURING CARDIOPULMONARY RESUSCITATION

FIELD OF THE INVENTION

The present invention relates generally to implantable cardiac monitoring and stimulation devices and, more particularly, to implantable cardiac monitoring and stimulation devices that employ pacing management during cardiopulmonary resuscitation.

BACKGROUND OF THE INVENTION

The healthy heart produces regular, synchronized contractions. Rhythmic contractions of the heart are normally controlled by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes. Ventricular fibrillation, for example, may be treated by delivering an electrical shock to the patient's heart through the use of a defibrillator.

Cardiopulmonary resuscitation (CPR) is commonly used to maintain life support for victims of cardiac arrest until a defibrillator can be deployed to treat the arrhythmia. In the absence of defibrillation therapy, the chances of surviving a cardiac arrest decrease rapidly as the duration of time following the arrest increases. Quick response to a cardiac arrest by performing CPR and subsequently administering a defibrillating shock is therefore of critical importance. The American Heart Association's "Chain of Survival," for example, recites the following steps:

1. Early access to emergency care, such as by activating an emergency medical system (EMS);
2. Early CPR initiated by a bystander or other first responder using basic life support (BLS) techniques to help the patient survive until more advanced care arrives;
3. Early defibrillation; and
4. Early advanced cardiac care.

The benefits of this approach are discussed in more detail in Cummins, et al. "Improving Survival From Sudden Cardiac Arrest: the 'Chain of Survival' Concept," 83 Circulation 1832-47 (May 1991).

EMS providers are playing an active role in implementing the Chain of Survival concept. Tiered EMS systems are emerging in many geographical areas and are typically divided between first responders, BLS providers, and ACLS (advanced cardiac life support) providers. First responders and BLS providers, often called EMT(B) or EMT-basic (emergency medical technician-basic), represent front line personnel who are first to reach a patient. Such personnel are now being trained and authorized to use automatic external defibrillators (AEDs) to provide early defibrillation.

Until the EMS provider arrives, CPR should be administered. Many people have been trained in CPR techniques, and are capable of performing CPR. However, although trained, many people never practice the techniques after initial training, and may be unsure of appropriate responses in an emergency, before the EMS provider arrives.

The compression during a CPR provides an external mechanical stimulation to the heart. Coordinating this mechanical stimulation with internal electrical stimulation of the heart may be beneficial to re-establishing normal sinus rhythm during a cardiac arrest.

SUMMARY OF THE INVENTION

The present invention is directed to systems and methods for coordinating cardiac pacing with delivery of cardiopulmonary resuscitation to a patient. Embodiments of the present invention are directed to methods and systems for managing cardiac pacing in a patient during CPR using a patient implantable medical device, and coordinating such cardiac pacing in concert with administration of CPR. In various embodiments, a patient implantable medical device is configured to orchestrate the administration of CPR using patient-externally perceivable prompts. In other embodiments, a device external of the patient, such as a programmer, is configured to orchestrate the administration of CPR using patient-externally perceivable prompts, such as by coordinating one or both of initiation and termination of CPR using appropriate prompts.

According to an embodiment, a method of managing cardiac pacing in a patient during a cardiac arrhythmia involves detecting a cardiac arrhythmia using the patient implantable medical device. The method further involves prompting a cardiopulmonary resuscitation compression and delivering, using the patient implantable medical device, a pacing pulse to a heart chamber in coordination with the compression prompt.

Delivering the pacing pulse to the heart chamber may involve detecting an onset of the cardiopulmonary resuscitation compression, and delivering the pacing pulse in response to the detected compression onset. Delivering the pacing pulse to the heart chamber may also involve detecting an acceleration of the patient implantable medical device, and delivering the pacing pulse in response to the detected acceleration. The method may involve delivering a pacing pulse to a heart chamber at a predetermined rate, and prompting the cardiopulmonary resuscitation compression by provision of a patient-externally audible prompt. Delivering the pacing pulse to the heart chamber may involve detecting a patient's transthoracic impedance using the patient implantable medical device, and delivering the pacing pulse in response to a change in the detected transthoracic impedance.

Prompting the cardiopulmonary resuscitation compression typically involves providing a patient-externally audible prompt. For example, prompting the cardiopulmonary resuscitation compression may involve providing a patient-externally audible prompt at a predetermined rate. By way of further example, prompting the cardiopulmonary resuscitation compression may involve prompting a cardiopulmonary resuscitation breath by provision of a patient-externally audible prompt distinct from that associated with prompting the cardiopulmonary resuscitation.

Prompting may involve prompting a first predetermined number of cardiopulmonary resuscitation breaths following provision of a second predetermined number of prompts for cardiopulmonary resuscitation compressions. Prompting may be adjusted or terminated in response to detecting cessation of the cardiac arrhythmia by, for example, detection of intracardiac electrogram or impedance signals.

According to another embodiment, a patient-implantable medical device includes a pacing circuit configured to deliver pacing pulses to a heart chamber, a sensing circuit configured to sense cardiac signals, and a prompting circuit configured for prompting a cardiopulmonary resuscitation compression. A processor is coupled to the pacing circuit, the sensing circuit, and the prompting circuit. The processor is configured to detect a cardiac arrhythmia using the sensing circuit, prompt a cardiopulmonary resuscitation compression, detect the onset of a cardiopulmonary resuscitation compression, and coordinate delivery of the pacing pulses to the heart chamber in coordination with the compression prompt.

The device may include an impedance sensing circuit coupled to the processor and configured to sense an impedance. In this configuration, the processor is configured to coordinate delivery of the pacing pulses to the heart chamber in response to detecting a change in the impedance. The device may include an accelerometer coupled to the processor and configured to sense an acceleration. In this configuration, the processor is configured to coordinate delivery of the pacing pulses to the heart chamber in response to detecting the acceleration.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
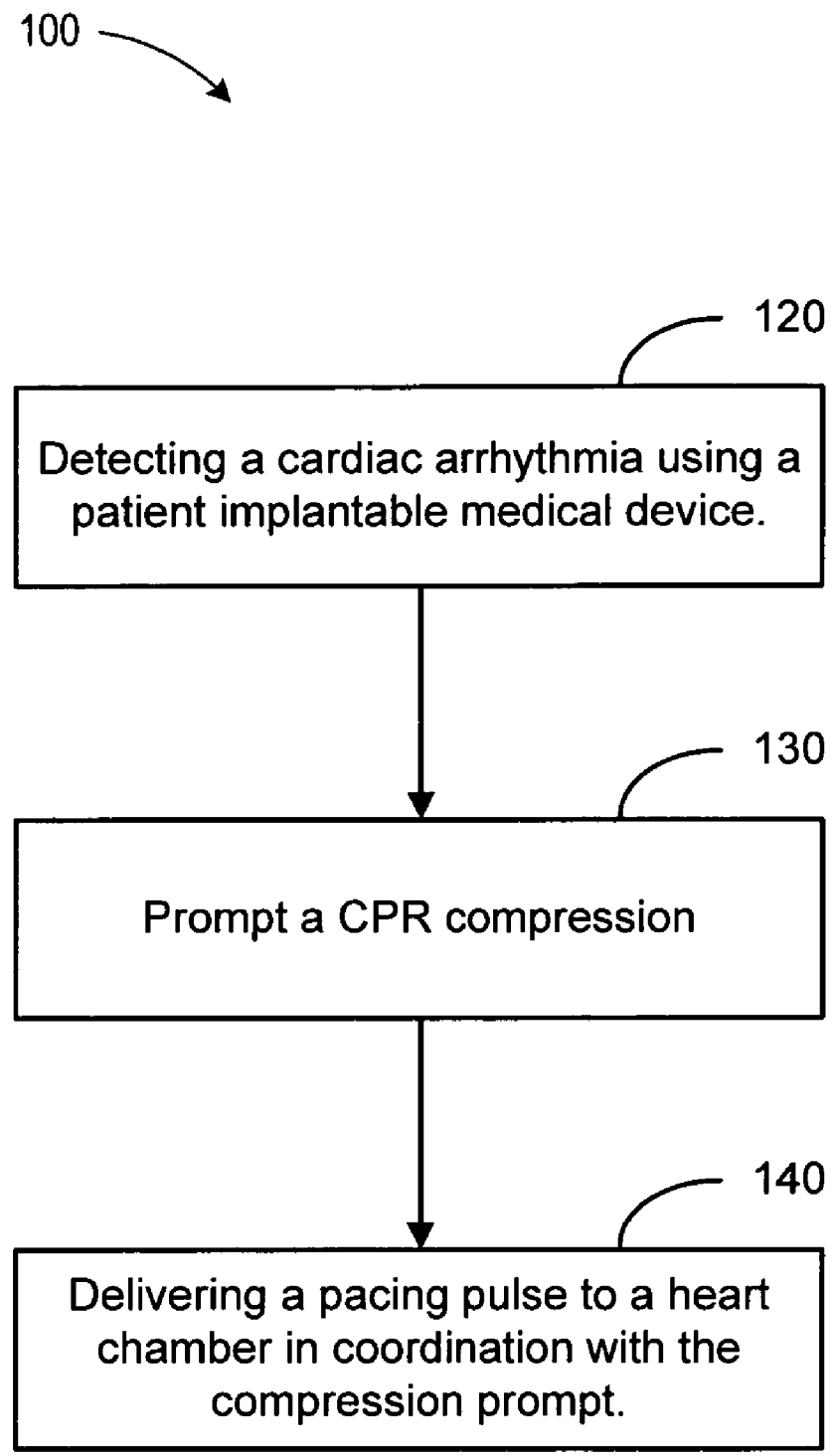
FIG. 1 is a flow chart illustrating coordination of electrical cardiac stimulation and the CPR process in accordance with embodiments of the present invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings, which form a part hereof, and in which is shown by way of illustration, various embodiments in which the invention may be practiced. It is to be understood that other embodiments may be utilized, and structural and functional changes may be made without departing from the scope of the present invention.

An implanted device in accordance with the present invention may include one or more of the features, structures, methods, or combinations thereof described hereinbelow. For example, a cardiac stimulator may be implemented to include one or more of the advantageous features and/or processes described below. It is intended that such a stimulator or other implanted or partially implanted device need not include all of the features described herein, but may be implemented to include selected features that provide for useful structures and/or functionality. Such a device may be implemented to provide a variety of therapeutic or diagnostic functions.

Implantable cardiac rhythm management systems have been used as an effective treatment for patients with serious arrhythmias, such as bradycardia and tachycardia conditions. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

A wide variety of implantable cardiac monitoring and/or stimulation devices may be configured to implement pacing management during cardiopulmonary resuscitation (CPR) in accordance with the present invention. A non-limiting, representative list of such devices includes cardiac monitors, pacemakers, cardiovertors, defibrillators, resynchronizers, and other cardiac monitoring and therapy delivery devices. These devices may be configured with a variety of electrode arrangements, including transvenous, endocardial, and epicardial electrodes (i.e., intrathoracic electrodes), and may also include subcutaneous, non-intrathoracic electrodes, including can, header, and indifferent electrodes, and subcutaneous array or lead electrodes (i.e., non-intrathoracic electrodes).

Embodiments of the present invention may be implemented in the context of a wide variety of cardiac devices, such as those listed above, and are referred to herein generally as a patient-internal medical devices (PIMDs) for convenience. A PIMD implemented in accordance with the present invention may incorporate one or more of the electrode types identified above, described below, incorporated by reference herein, and combinations thereof.

Pacing management during CPR in accordance with the present invention may be implemented with a PIMD. According to various embodiments, the can of the PIMD may be implemented to reside outside the ribcage as in the case of a pacemaker, cardiac resynchronization therapy (CRT) device, or ICD. One or more leads incorporating electrodes may be located in direct contact with the heart, great vessel or coronary vasculature, such as via one or more leads implanted by use of conventional transvenous or epicardial delivery approaches. In other implementations, one or more electrode subsystems or electrode arrays may be used to sense cardiac activity and deliver cardiac stimulation energy in a PIMD configuration employing an active can or a configuration employing a non-active can. Electrodes may be situated at anterior and/or posterior locations relative to the heart.

According to other embodiments, the PIMD may be implanted subcutaneously such that all or selected elements of the device are positioned on the patient's front, back, side, or other body locations suitable for sensing cardiac activity and delivering cardiac stimulation therapy. The primary housing (e.g., the active or non-active can) of the PIMD, for example, may be configured for positioning outside of the rib cage at an intercostal or subcostal location, within the abdomen, or in the upper chest region (e.g., subclavian location, such as above the third rib). In one implementation, one or more electrodes may be located on the primary housing and/or at other locations about, but not in direct contact with the heart, great vessel or coronary vasculature. A variety of other PIMD configurations are contemplated that may be implemented in accordance with the principles of the present invention.

The present invention is directed to pacing management, using a PIMD, during CPR. Aspects of the invention involve methods and systems that facilitate coordinated delivery of electrical cardiac stimulation and CPR processes. The orchestration of electrical cardiac stimulation and manual steps of the CPR process provides for enhanced feedback during cardiac arrest that significantly increases the efficacy of CPR delivery.

Implementing a PIMD in accordance with the present invention advantageously enhances mechano-electric feedback during cardiac arrest to regain electrical-mechanical association of the patient's cardiac activity. For example, ventricular fibrillation is an example of an electro-mechanical disassociation event, where the mechanical pumping of the heart is disassociated with the electrical stimulation of the myocardium. Coordinating electrical cardiac stimulation and the CPR process using a PIMD in accordance with the present invention improves CPR efficacy, and may possibly work to restore normal sinus rhythm without defibrillation in select cases.

By way of further example, and in the context of the PIMD implemented as an ICD and the rare scenario where the PIMD is not effective in rescuing the patient, the ICD may be programmed to automatically disable shock therapy delivery on a temporary basis during the time CPR is being administered. In particular, the ICD may be programmed to temporarily disable shock therapy delivery if the ICD detects that CPR is being administered to the patient, such as by detecting CPR compressions in a manner described herein. Temporarily disabling shock therapy delivery is intended to provide a measure of safety against high voltage shocks for the giver of CPR. Shock therapy is automatically enabled upon the ICD detecting the termination of CPR compressions.

FIG. 1 is a flow chart illustrating a method 100 of coordinating electrical cardiac stimulation and CPR delivery in accordance with embodiments of the present invention. The method 100 involves detecting 120 a cardiac arrhythmia using a patient implantable medical device. A CPR compression is prompted 130, and a pacing pulse is delivered 140 to a heart chamber in coordination with the compression prompt using the patient implantable medical device.

Prompting 130 may be accomplished in several ways, such as by enunciating an audible signal from the PIMD that is perceivable externally of the patient. The PIMD may include an audio enunciation capability, such as a speaker system, a buzzer, clicker, or other sound producing or projecting system that provides a patient-externally perceivable audio prompt. For example, a beep, buzz, tone, tone-burst, or other prompt may be enunciated.

Using, for discussion purposes, a beep as an example of the prompt 130, the PIMD may be programmed to beep using a first tone at a first predetermined repetition rate, such as about 100 beeps per minute, for a predetermined number of beeps, such as about 15 beeps. After 15 beeps, the prompt 130 may change tone, and beep at the changed tone at a second predetermined repetition rate, such as about 60 beeps per minute, for a second predetermined number of beeps, such as about 2 beeps, corresponding to the breathing phase of the CPR. The PIMD may then return to the first tone, and repeat the cycle corresponding to the CPR process.

Figure 2:
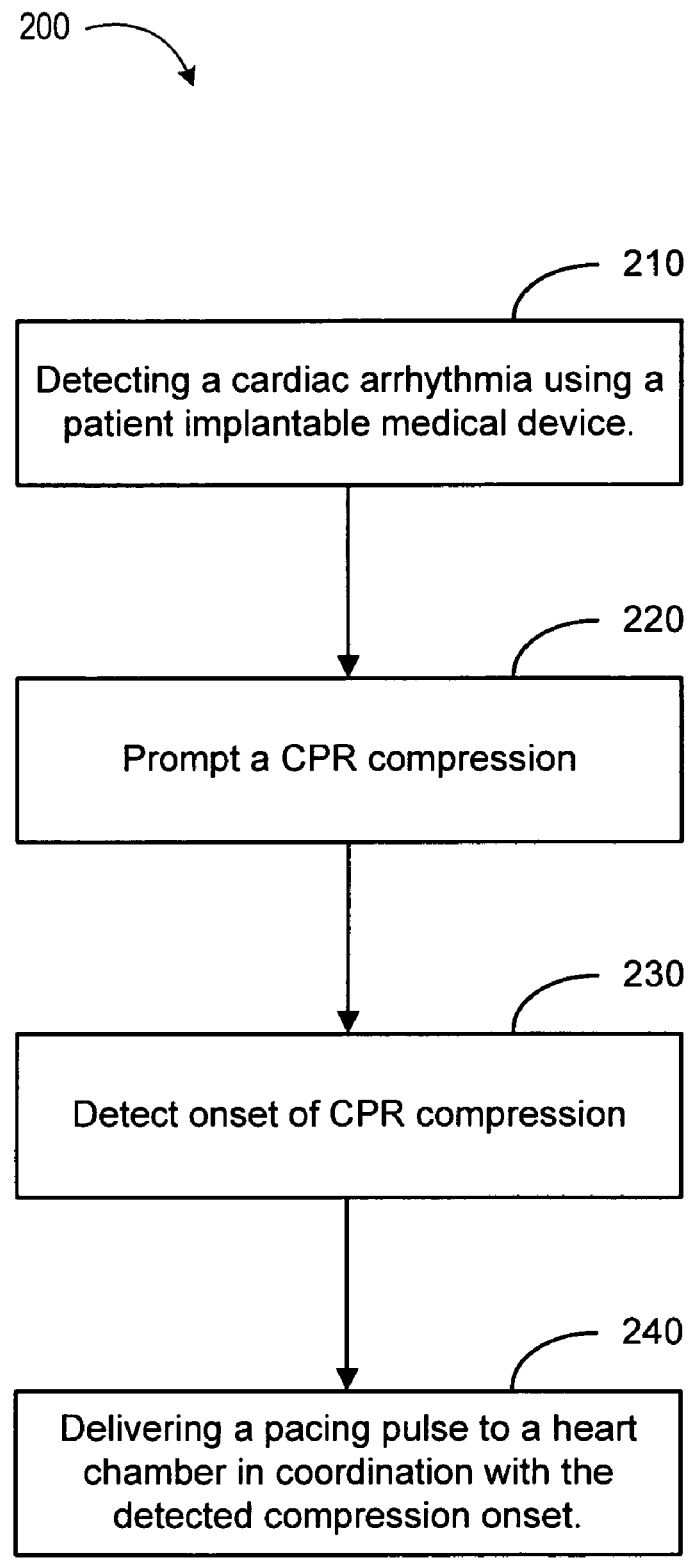
FIG. 2 is a flow chart illustrating a method of coordinating electrical cardiac stimulation and the CPR process in accordance with other embodiments of the present invention.

FIG. 2 is a flow chart illustrating a method 200 that facilitates coordinated electrical cardiac stimulation and CPR delivery in accordance with other embodiments of the present invention. The method 200 involves detecting 210 a cardiac arrhythmia using a patient implantable medical device. A CPR compression is prompted 220. A CPR compression is detected 230, and a pacing pulse is delivered 240 to a heart chamber in coordination with detection 230 of the CPR compression.

For example, an accelerometer, pressure transducer, transthoracic impedance sensor or other sensor suitable for detection 230 of chest compression may be used to detect the onset of the CPR compression. Pacing pulse delivery 240 is coordinated with the detection 230 of chest compression associated with the onset of CPR delivery. In embodiments involving coordination between the pacing pulse delivery 240 and the CPR compression detection 230, pacing pulse delivery 240 may be initiated in response to detecting an increase in chest pressure above a predetermined threshold, such as by detecting a change in a pressure transducer output signal, a change in acceleration detected by an accelerometer, or a change beyond a predetermined threshold by any sensor suitable to detect 230 the CPR compression.

In another embodiment involving coordination between pacing pulse delivery 240 and CPR compression detection 230, pacing pulse delivery 240 may be initiated based on a measured timing interval between the prompt event 220 and the CPR compression detected 230 from a previous compression, such that the time lag of the person performing the CPR from the prompt 220 may be mitigated, and such that the CPR compression may be properly timed with the pacing pulse delivery 240.

Figure 3:
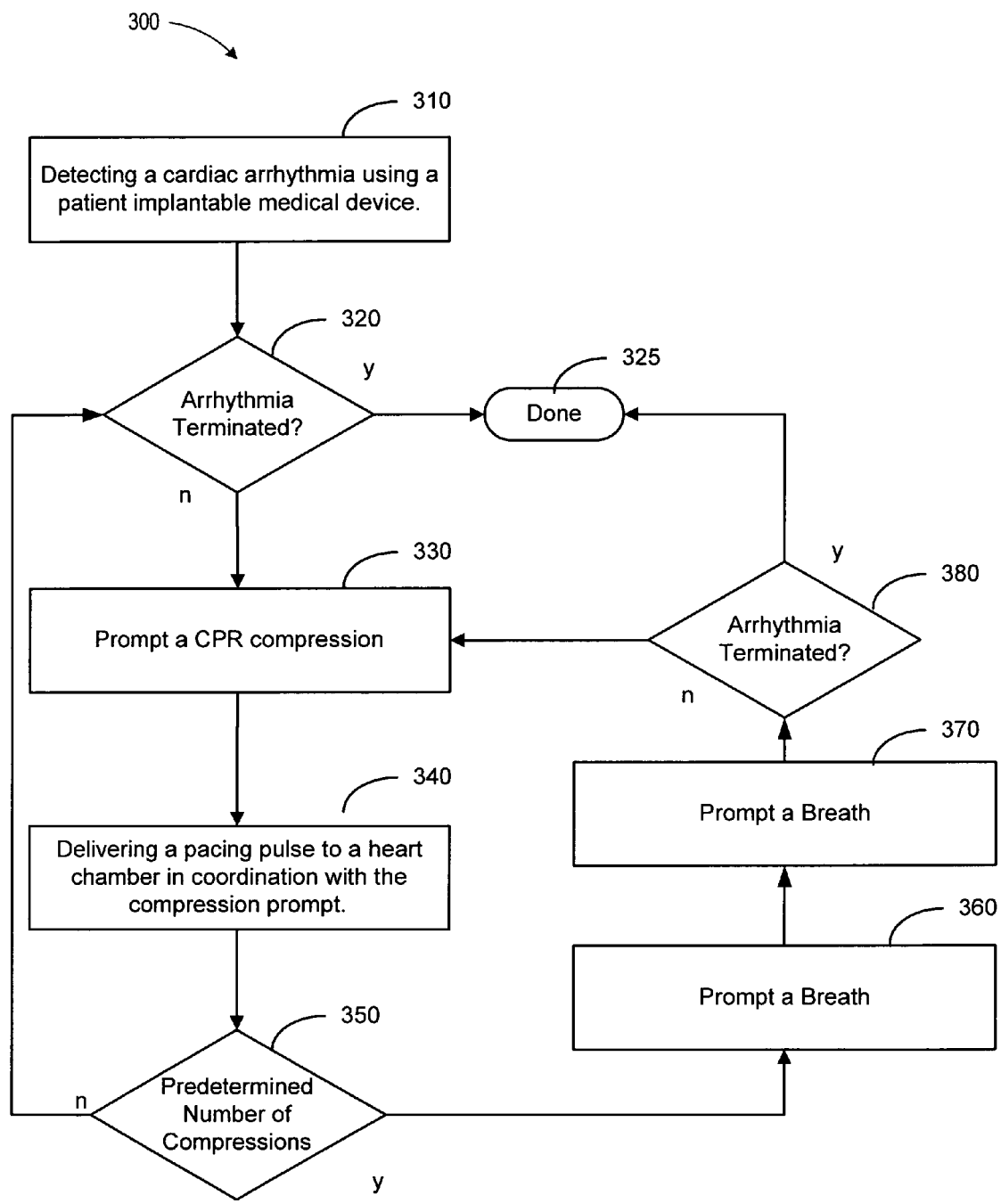
FIG. 3 is a flow chart illustrating a method of coordinating electrical cardiac stimulation and the CPR process in accordance with further embodiments of the present invention.

FIG. 3 is a flow chart illustrating a method 300 that facilitates coordinated electrical cardiac stimulation and CPR delivery in accordance with further embodiments of the present invention. The method 300 involves detecting 310 a cardiac arrhythmia using a patient implantable medical device. A check 320 is made to determine if the arrhythmia has been terminated. If the arrhythmia is terminated, then the method 300 is also terminated 325. If the arrhythmia is not terminated, a CPR compression is prompted 330 and a pacing pulse is delivered 340 to a heart chamber in coordination with the compression prompt using the patient implantable medical device.

A check 350 is made to determine if a predetermined number (e.g., 15) of CPR compressions 330 have been prompted 330. If the result of determination 350 is NO, then the method returns to check 320 and steps 320, 330, 340, 350 are repeated until the arrhythmia has been terminated or the predetermined number of CPR compressions has been reached. If determination 350 finds that the predetermined number of CPR compressions has been reached, then a first breath 360 is prompted followed by a second breath 370 upon expiration of the predetermined time interval following the first breath prompt 360. A check 380 is made for termination of the arrhythmia, and the method 300 continues or terminates 325 based on the check 380.

It is understood that, according the above example, more or less than 15 CPR compression prompts may be made, and more or less than two breaths may be prompted without departing from the scope of the present invention. Further, it is understood that checking for arrhythmia termination may occur continuously or periodically during the CPR delivery process exemplified in FIG. 3.

Figure 4:
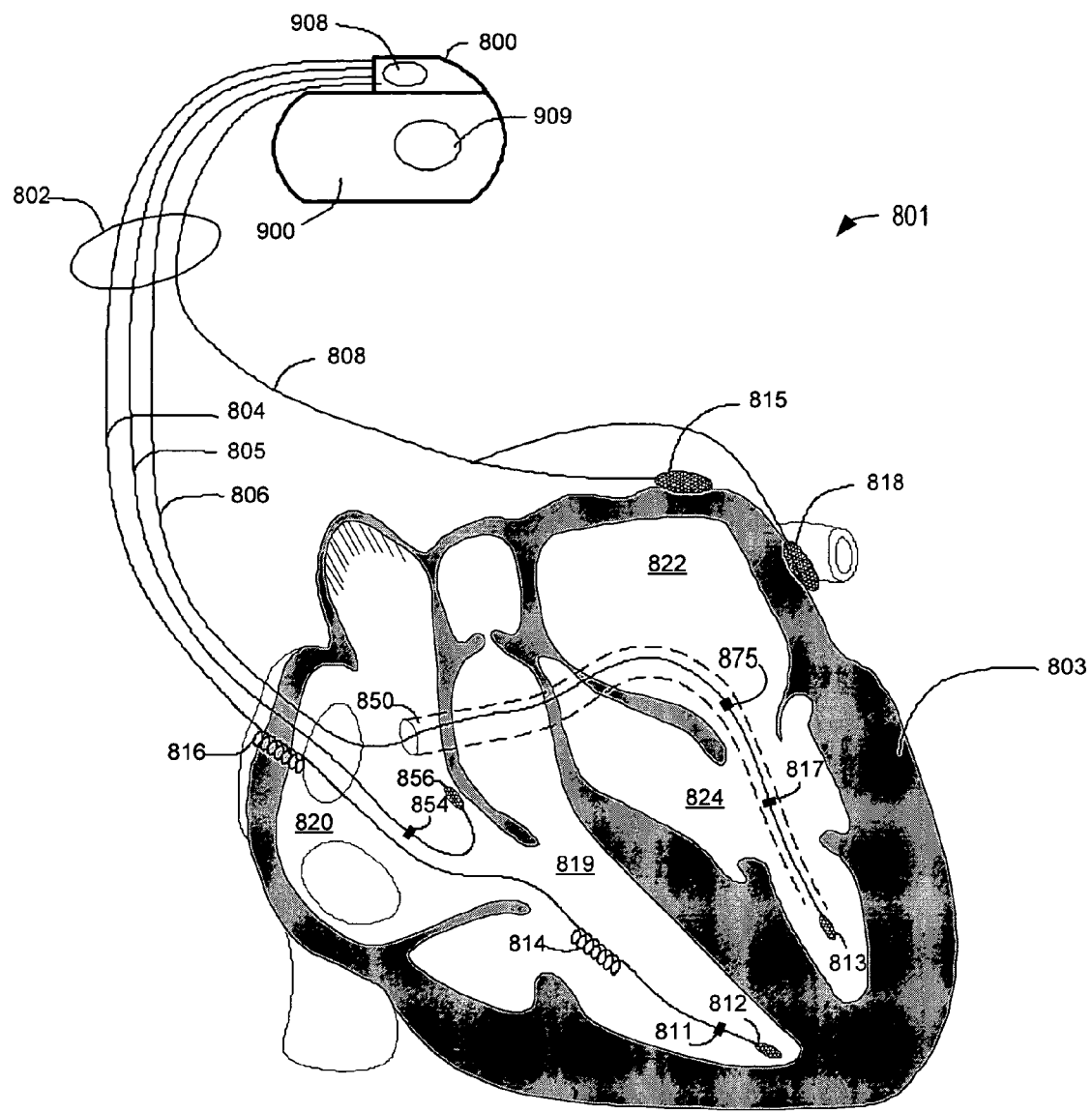
FIG. 4 is a view of a heart and an apparatus that provides for coordinated electrical cardiac stimulation and the CPR delivery in accordance with embodiments of the present invention.

Turning now to FIG. 4, a system in accordance with an embodiment of the present invention is shown having a lead system deployed within a heart. A PIMD system 801 includes a PIMD 800 with a lead system 802 that is designed for implantation in a coronary vein for purposes of cardiac resynchronization therapy (CRT), according to this embodiment. The lead system 802 is coupled to a detection/energy delivery system 900 (shown in detail in FIG. 5) that actively measures and controls the implanted lead system to provide cardiac pacing therapy to a patient's heart 803.

The detector/energy delivery system 900 typically includes a power supply and programmable circuit (e.g., microprocessor) coupled to an analog to digital (A-D) converter. Various lead system devices, such as electrodes and pressure sensors, can interface to the A-D converter for sensing/data collection. Alternatively, analog conditioning (e.g., filtering) may be applied to sensor signals before interfacing with the A-D converter. The detector/energy delivery system 900 also utilizes an energy delivery system. The energy delivery system may include charge capacitors and signal conditioning circuitry known in the art. The energy system may interface to the programmable circuit through a D-A converter. Components and functionality of the detector/energy delivery system 900 will be further described below with reference to FIG. 5.

Still referring to FIG. 4, the lead system 802 may be implanted into the coronary sinus using various techniques. One such technique, as illustrated in FIG. 4, involves creating an opening in a percutaneous access vessel such as the left subclavian or left cephalic vein. The pacing lead is guided into a right atrial chamber 820 of the heart via the superior vena cava. From the right atrial chamber 820, the lead system 802 is sent into the coronary sinus ostium. The ostium is the opening of a coronary sinus 850 into the right atrial chamber 820. The lead system 802 is guided through the coronary sinus 850 to a coronary vein of the left ventricle 824. A distal end of the lead system 802 may be lodged into the coronary vein.

Referring still to FIG. 4 of the drawings, the PIMD system 801 may be used to implement methods for pacing management during CPR in accordance with the present invention. The PIMD system 801 in FIG. 4 is illustrated having the PIMD 800 electrically and physically coupled to the lead system 802. The housing and/or header of the PIMD 800 may incorporate one or more electrodes 908, 909 used to provide electrical stimulation energy to the heart and to sense cardiac electrical activity. The PIMD 800 may utilize all or a portion of the PIMD housing as a can electrode 909. The PIMD 800 may include an indifferent electrode positioned, for example, on the header or the housing of the PIMD 800. If the PIMD 800 includes both a can electrode 909 and an indifferent electrode 908, the electrodes 908, 909 typically are electrically isolated from each other.

The lead system 802 may include intracardiac leads 804, 805, 806 implanted in a human body with portions of the intracardiac leads 804, 805, 806 inserted into a heart 803. The intracardiac leads 804, 805, 806 include various electrodes positionable within the heart for sensing electrical activity of the heart and for delivering electrical stimulation energy to the heart, for example, pacing pulses and/or defibrillation shocks under certain predetermined conditions to treat cardiac arrhythmias. The lead system 802 may include one or more electrodes used for pacing, sensing, and/or defibrillation.

In the embodiment shown in FIG. 4, the lead system 802 includes an intracardiac right ventricular (RV) lead system 804, an intracardiac right atrial (RA) lead system 805, an intracardiac left ventricular (LV) lead system 806, and an extracardiac left atrial (LA) lead system 808. The lead system 802 of FIG. 4 illustrates one embodiment that may be used in connection with pacing management during CPR methodologies described herein. Other leads and/or electrodes may additionally or alternatively be used. As illustrated in FIG. 4, for example, the lead system 802 may include one or more extracardiac leads 808 having electrodes, e.g., epicardial electrodes or sensors 815, 818, positioned at locations outside the heart for sensing and/or pacing one or more heart chambers.

The right ventricular lead system 804 illustrated in FIG. 4 includes an SVC-coil 816, an RV-coil 814, an RV-ring electrode 811, and an RV-tip electrode 812. The right ventricular lead system 804 extends through the right atrium 820 and into the right ventricle 819. In particular, the RV-tip electrode 812, RV-ring electrode 811, and RV-coil electrode 814 are positioned at appropriate locations within the right ventricle 819 for sensing and delivering electrical stimulation pulses to the heart. The SVC-coil 816 is positioned at an appropriate location within the right atrium chamber 820 of the heart 803 or a major vein leading to the right atrial chamber 820 of the heart 803.

In one configuration, the RV-tip electrode 812 referenced to the can electrode 909 may be used to implement unipolar pacing and/or sensing in the right ventricle 819. Bipolar pacing and/or sensing in the right ventricle may be implemented using the RV-tip 812 and RV-ring 811 electrodes. In yet another configuration, the RV-ring 811 electrode may optionally be omitted, and bipolar pacing and/or sensing may be accomplished using the RV-tip electrode 812 and the RV-coil 814, for example. The right ventricular lead system 804 may be configured as an integrated bipolar pace/shock lead. The RV-coil 814 and the SVC-coil 816 are defibrillation electrodes.

The left ventricular lead 806 includes an LV distal electrode 813 and an LV proximal electrode 817 located at appropriate locations in or about the left ventricle 824 for pacing and/or sensing the left ventricle 824. The left ventricular lead 806 may be guided into the right atrium 820 of the heart via the superior vena cava. From the right atrium 820, the left ventricular lead 806 may be deployed into the coronary sinus ostium, the opening of the coronary sinus 850. The lead 806 may be guided through the coronary sinus 850 to a coronary vein of the left ventricle 824. This vein is used as an access pathway for leads to reach the surfaces of the left ventricle 824 which are not directly accessible from the right side of the heart. Lead placement for the left ventricular lead 806 may be achieved via subclavian vein access and a preformed guiding catheter for insertion of the LV electrodes 813, 817 adjacent to the left ventricle.

Unipolar pacing and/or sensing in the left ventricle may be implemented, for example, using the LV distal electrode referenced to the can electrode 909. The LV distal electrode 813 and the LV proximal electrode 817 may be used together as bipolar sense and/or pace electrodes for the left ventricle. The left ventricular lead 806 and the right ventricular lead 804, in conjunction with the PIMD 800, may be used to provide cardiac resynchronization therapy such that the ventricles of the heart are paced substantially simultaneously, or in phased sequence, for patients suffering from chronic heart failure.

The right atrial lead 805 includes a RA-tip electrode 856 and an RA-ring electrode 854 positioned at appropriate locations in the right atrium 820 for sensing and pacing the right atrium 820. In one configuration, the RA-tip 856 referenced to the can electrode 909, for example, may be used to provide unipolar pacing and/or sensing in the right atrium 820. In another configuration, the RA-tip electrode 856 and the RA-ring electrode 854 may be used to provide bipolar pacing and/or sensing.

The left ventricular lead 806, as shown in FIG. 4, may include a pressure transducer 809. The pressure transducer 809 used in this application can be a micro-electrical-mechanical system (MEMS), for example. The pressure transducer 809 can include a micromachined capacitive or piezoresistive transducer exposed to the bloodstream. Other pressure transducer technologies, such as resistive strain gages, are known in the art and can also be employed as a pressure transducer 809. The pressure transducer 809 is coupled to one or more conductors disposed along the length of the left ventricular lead 806. In the configuration shown in FIG. 4, the pressure transducer 809 is integrated with the left ventricular lead 806.

Figure 5:
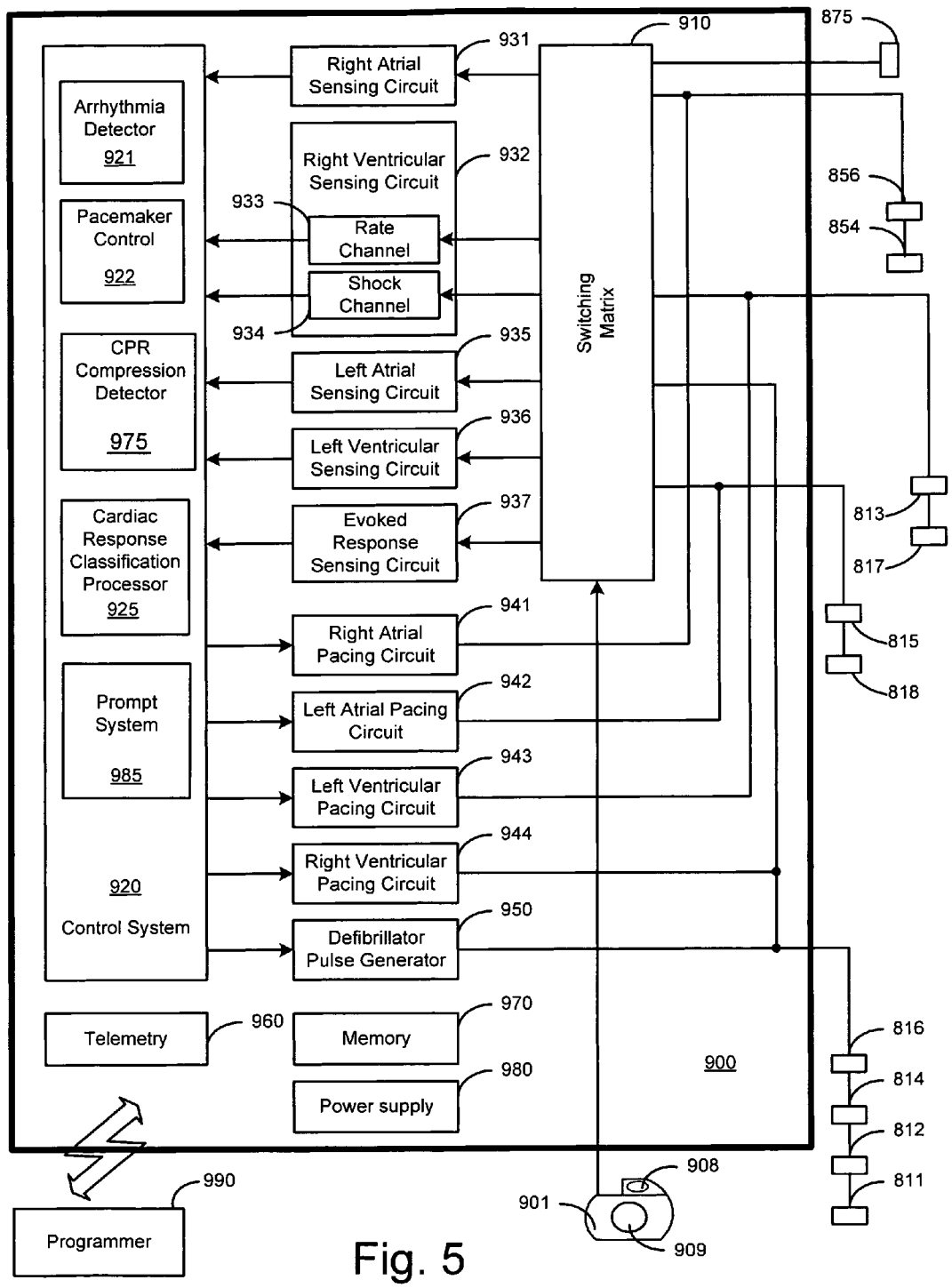
FIG. 5 is a block diagram of a system configured to facilitate coordinated electrical cardiac stimulation and the CPR delivery in accordance with embodiments of the present invention.

Referring now to FIG. 5, there is shown an embodiment of a PIMD 900 suitable for providing pacing management during CPR in accordance with the present invention. FIG. 5 shows the PIMD 900 divided into functional blocks. It is understood by those skilled in the art that there exist many possible configurations in which these functional blocks can be arranged. The example depicted in FIG. 5 is one possible functional arrangement. Other arrangements are also possible. For example, more, fewer or different functional blocks may be used to describe a PIMD suitable for implementing the methodologies for adaptive windowing in accordance with the present invention. In addition, although the PIMD 900 depicted in FIG. 5 contemplates the use of a programmable microprocessor-based logic circuit, other circuit implementations may be utilized.

The PIMD 900 depicted in FIG. 5 includes circuitry for receiving cardiac signals from a heart and delivering electrical stimulation energy to the heart in the form of pacing pulses and/or defibrillation shocks. In one embodiment, the circuitry of the PIMD 900 is encased and hermetically sealed in a housing 901 suitable for implanting in a human body. Power to the PIMD 900 is supplied by an electrochemical battery 980. A connector block (not shown) is attached to the housing 901 of the PIMD 900 to allow for the physical and electrical attachment of the lead system conductors to the circuitry of the PIMD 900.

The PIMD 900 may be a programmable microprocessor-based system, including a control system 920 and a memory 970. The memory 970 may store parameters for various pacing, defibrillation, and sensing modes, along with other parameters. Further, the memory 970 may store data indicative of signals received by other components of the PIMD 900. The memory 970 may be used, for example, for storing historical EGM, and/or therapy data. The historical data storage may include, for example, data obtained from long-term patient monitoring used for trending or other diagnostic purposes. Historical data, as well as other information, may be transmitted to an external programmer unit 990 as needed or desired.

The control system 920 and memory 970 may cooperate with other components of the PIMD 900 to control the operations of the PIMD 900. The control system depicted in FIG. 5 incorporates a template creation and matching processor 925 for classifying cardiac responses to pacing stimulation. The control system 920 may include additional functional components including a pacemaker control circuit 922, an arrhythmia detector 921, and a template processor for cardiac signal morphology analysis, along with other components for controlling the operations of the PIMD 900.

CPR compression detector 975 is provided, and may be implemented as specialized circuitry configured to detect CPR compressions, or may be implemented as software, firmware, or combination of hardware and software. For example, the CPR compression detector 975 may use an impedance sensor, a pressure transducer, an accelerometer, or other suitable sensor. A prompt system 985 is also provided to prompt CPR in accordance with the present invention. As described earlier, the prompt system 985 may be implemented as a speaker system, buzzer, vibrator, or other prompting arrangement.

Telemetry circuitry 960 may be implemented to provide communications between the PIMD 900 and an external programmer unit 990 or other patient-external system or device. In one embodiment, the telemetry circuitry 960 and the programmer unit 990 communicate using a wire loop antenna and a radio frequency telemetric link, as is known in the art, to receive and transmit signals and data between the programmer unit 990 and the telemetry circuitry 960. In this manner, programming commands and other information may be transferred to the control system 920 of the PIMD 900 from the programmer unit 990 during and after implant. In addition, stored cardiac data pertaining to coordination between electrical cardiac stimulation and CPR compression, for example, along with other data, may be transferred to the programmer unit 990 from the PIMD 900. This data may be used to refine or adjust PIMD parameters implicated during coordinated pacing management and CPR delivery.

In the embodiment of the PIMD 900 illustrated in FIG. 4, electrodes RA-tip 856, RA-ring 854, RV-tip 812, RV-ring 811, RV-coil 814, SVC-coil 816, LV distal electrode 813, LV proximal electrode 817, LA distal electrode 818, LA proximal electrode 815, indifferent electrode 908, and can electrode 909 are coupled through a switch matrix 910 to sensing circuits 931-937.

A right atrial sensing circuit 931 serves to detect and amplify electrical signals from the right atrium of the heart. Bipolar sensing in the right atrium may be implemented, for example, by sensing voltages developed between the RA-tip 856 and the RA-ring 854. Unipolar sensing may be implemented, for example, by sensing voltages developed between the RA-tip 856 and the can electrode 909. Outputs from the right atrial sensing circuit are coupled to the control system 920.

A right ventricular sensing circuit 932 serves to detect and amplify electrical signals from the right ventricle of the heart. The right ventricular sensing circuit 932 may include, for example, a right ventricular rate channel 933 and a right ventricular shock channel 934. Right ventricular cardiac signals sensed through use of the RV-tip 812 electrode are right ventricular near-field signals and are denoted RV rate channel signals. A bipolar RV rate channel signal may be sensed as a voltage developed between the RV-tip 812 and the RV-ring 811. Alternatively, bipolar sensing in the right ventricle may be implemented using the RV-tip electrode 812 and the RV-coil 814. Unipolar rate channel sensing in the right ventricle may be implemented, for example, by sensing voltages developed between the RV-tip 812 and the can electrode 909.

Right ventricular cardiac signals sensed through use of the RV-coil electrode 814 are far-field signals, also referred to as RV morphology or RV shock channel signals. More particularly, a right ventricular shock channel signal may be detected as a voltage developed between the RV-coil 814 and the SVC-coil 816. A right ventricular shock channel signal may also be detected as a voltage developed between the RV-coil 814 and the can electrode 909. In another configuration the can electrode 909 and the SVC-coil electrode 816 may be electrically shorted and a RV shock channel signal may be detected as the voltage developed between the RV-coil 814 and the can electrode 909/SVC-coil 816 combination.

Left atrial cardiac signals may be sensed through the use of one or more left atrial electrodes 815, 818, which may be configured as epicardial electrodes. A left atrial sensing circuit 935 serves to detect and amplify electrical signals from the left atrium of the heart. Bipolar sensing and/or pacing in the left atrium may be implemented, for example, using the LA distal electrode 818 and the LA proximal electrode 815. Unipolar sensing and/or pacing of the left atrium may be accomplished, for example, using the LA distal electrode 818 to can vector 909 or the LA proximal electrode 815 to can vector 909.

Referring still to FIG. 5, a left ventricular sensing circuit 936 serves to detect and amplify electrical signals from the left ventricle of the heart. Bipolar sensing in the left ventricle may be implemented, for example, by sensing voltages developed between the LV distal electrode 813 and the LV proximal electrode 817. Unipolar sensing may be implemented, for example, by sensing voltages developed between the LV distal electrode 813 or the LV proximal electrode 817 and the can electrode 909.

Optionally, an LV coil electrode (not shown) may be inserted into the patient's cardiac vasculature, e.g., the coronary sinus, adjacent the left heart. Signals detected using combinations of the LV electrodes, 813, 817, LV coil electrode (not shown), and/or can electrodes 909 may be sensed and amplified by the left ventricular sensing circuitry 936. The output of the left ventricular sensing circuit 936 is coupled to the control system 920.

In particular configurations, systems and methods of the present invention may perform various pacing therapies as are known in the art. Exemplary pacemaker circuitry, structures and functionality, aspects of which may be incorporated in a PIMD of a type that may benefit from pacing management during CPR, are disclosed in commonly owned U.S. Pat. Nos. 4,562,841; 5,284,136; 5,376,106; 5,036,849; 5,540,727; 5,836,987; 6,044,298; and 6,055,454, and U.S. Publication No. 2004/0230249, which are hereby incorporated herein by reference.

A PIMD in accordance with the present invention may implement diagnostic and/or monitoring functions as well as provide cardiac stimulation therapy. Exemplary cardiac monitoring circuitry, structures and functionality, aspects of which may be incorporated in a PIMD of a type that may benefit from pacing management during CPR in accordance with the present invention, are disclosed in commonly owned U.S. Pat. Nos. 5,313,953; 5,388,578; and 5,411,031, which are hereby incorporated herein by reference.

A PIMD may be used to implement various diagnostic functions, which may involve performing rate-based, pattern and rate-based, and/or morphological tachyarrhythmia discrimination analyses. Subcutaneous, cutaneous, and/or external sensors may be employed to acquire physiologic and non-electrophysiological information for purposes of enhancing tachyarrhythmia detection and termination. It is understood that configurations, features, and combination of features described in the present disclosure may be implemented in a wide range of implantable medical devices, and that such embodiments and features are not limited to the particular devices described herein.

A PIMD may incorporate circuitry, structures and functionality of the subcutaneous implantable medical devices disclosed in commonly owned U.S. Pat. Nos. 5,203,348; 5,230,337; 5,360,442; 5,366,496; 5,397,342; 5,391,200; 5,545,202; 5,603,732; and 5,916,243, which are hereby incorporated herein by reference.

Various PIMD embodiments described herein may be used in connection with advanced patient management. Methods, structures, and/or techniques described herein, which may be adapted to provide for remote patient/device monitoring, diagnosis, therapy, or other APM related methodologies, may incorporate features of one or more of the following references: U.S. Pat. Nos. 6,221,011; 6,270,457; 6,277,072; 6,280,380; 6,312,378; 6,336,903; 6,358,203; 6,368,284; 6,398,728; and 6,440,066, which are hereby incorporated herein by reference.

Various modifications and additions can be made to the preferred embodiments discussed hereinabove without departing from the scope of the present invention. For example, a PIMD may include communication circuitry that communicates a prompt signal to a patient-external device that can reproduce an audible or visual prompt. A PIMD may communicate a prompt signal to a cellular phone, key chain transceiver, wristwatch, medical alert bracelet equipped with a communications interface, or other device that is configured to receive and reproduce a prompt signal from the PIMD. In such configurations, the PIMD need not incorporate an audible projection system, but may instead rely on the external device to reproduce an audible or visual prompt to the giver of CPR therapy. In other configurations, such external reproducing devices of a prompt signal may supplement the audible projection system of the PIMD to provide for enhanced prompt signal projection in high ambient noise environments. Accordingly, the scope of the present invention should not be limited by the particular embodiments described above, but should be defined only by the claims set forth below and equivalents thereof.

What is claimed is:

1. A method of managing cardiac pacing in a patient during a cardiac arrhythmia using a patient implantable medical device, comprising:

detecting a cardiac arrhythmia using a patient implantable medical device;

detecting a plurality of cardiopulmonary resuscitation compressions using the patient implantable medical device, the plurality of cardiopulmonary resuscitation compressions human delivered, and delivering, using the patient implantable medical device, a plurality of pacing pulses sufficient to capture tissue of a heart chamber to the patient's heart in timed relation to detection of the cardiopulmonary resuscitation compressions, each pulse of the plurality delivered in response to detection of a respective cardiopulmonary resuscitation compression of the plurality.

2. The method of claim 1, further comprising prompting each of the cardiopulmonary resuscitation compressions in response to detection of the cardiac arrhythmia.

3. The method of claim 1, wherein:
detecting the cardiopulmonary resuscitation compressions comprises detecting accelerations of the patient implantable medical device; and
delivering the pacing pulses to the heart chamber comprises delivering an individual pacing pulse in response to detection of each acceleration.

4. The method of claim 1, wherein:
detecting the cardiopulmonary resuscitation compressions comprises detecting onset of each of the cardiopulmonary resuscitation compressions; and
delivering the pacing pulses to the heart chamber comprises initiating an individual pacing pulse to the heart chamber in response to each detection of onset of compression.

5. The method of claim 1, wherein:
detecting the cardiopulmonary resuscitation compressions comprises detecting changes in the patient's transthoracic impedance using the patient implantable medical device, wherein each pulse of the plurality is delivered in response to a respective detected change in the patient's transthoracic impedance.

6. The method of claim 2, wherein prompting the cardiopulmonary resuscitation compressions comprises providing a patient-externally audible prompt for each compression.

7. The method of claim 2, wherein prompting the cardiopulmonary resuscitation compressions comprises providing a patient-externally audible prompt at a predetermined rate.

8. The method of claim 2, wherein prompting the cardiopulmonary resuscitation compressions further comprises prompting at least one cardiopulmonary resuscitation breath by provision of a patient-externally audible prompt distinct from that associated with prompting the cardiopulmonary resuscitations.

9. The method of claim 2, comprising adjusting or terminating the prompting in response to detecting cessation of the cardiac arrhythmia.

10. A patient-implantable medical device, comprising:
a housing configured for implantation;
a pacing circuit configured to deliver a plurality of pacing pulses sufficient to capture cardiac tissue to a heart chamber, the pacing circuit contained at least partially within the housing;
a sensing circuit configured to sense cardiac signals, the sensing circuit contained at least partially within the housing;
a cardiopulmonary resuscitation compression circuit configured to detect delivery of a plurality of human delivered cardiopulmonary resuscitation compressions, the cardiopulmonary resuscitation compression circuit contained at least partially within the housing; and
a processor coupled to the pacing circuit, the sensing circuit, and the cardiopulmonary resuscitation compression circuit, the processor configured to detect a cardiac arrhythmia using the sensing circuit, detect the plurality of cardiopulmonary resuscitation compressions, and coordinate delivery of the plurality of pacing pulses to the heart chamber such that each pulse of the plurality is delivered in response to detection of a respective cardiopulmonary resuscitation compression of the plurality.

11. The device of claim 10, wherein the cardiopulmonary resuscitation compression circuit comprises an impedance sensing circuit coupled to the processor and configured to sense an impedance signal indicative of the cardiopulmonary resuscitation compressions.

12. The device of claim 10, wherein the cardiopulmonary resuscitation compression circuit comprises an accelerometer coupled to the processor and configured to sense an acceleration signal indicative of each of the cardiopulmonary resuscitation compressions.

13. The device of claim 10, further comprising a prompting circuit configured to prompt delivery of the cardiopulmonary resuscitation compressions in response to detection of the cardiac arrhythmia.

14. The device of claim 13, wherein the processor is configured to prompt a cardiopulmonary resuscitation breath at a predetermined rate following a predetermined number of prompts for cardiopulmonary resuscitation compressions.

15. The device of claim 10, wherein the processor is configured to detect onset of each cardiopulmonary resuscitation compression and initiate delivery of a respective one of the pacing pulses in response to detection of onset of each cardiopulmonary resuscitation compression of the plurality.

16. A patient-implantable medical device for managing cardiac pacing in a patient during a cardiac arrhythmia, comprising:
means for implantably detecting a cardiac arrhythmia;
means for implantably detecting a plurality of cardiopulmonary resuscitation compressions, the plurality of cardiopulmonary resuscitation compressions human delivered; and
means for implantably delivering a plurality of pacing pulses sufficient to capture cardiac tissue to a heart chamber in timed relation to detection of the cardiopulmonary resuscitation compressions, each pulse of the plurality delivered in response to detection of a respective cardiopulmonary resuscitation compression of the plurality.

17. The device of claim 16, comprising means for detecting an onset of each of the cardiopulmonary resuscitation compressions, wherein the pacing pulse delivery means is configured to initiate delivery of the pacing pulses in response to detection of compression onset such that each pulse of the plurality is delivered in response to detection of onset of a respective cardiopulmonary resuscitation compression of the plurality.

18. The device of claim 16, comprising means for detecting an acceleration of the patient implantable medical device.

19. The device of claim 16, comprising means for detecting electro-mechanical association of the cardiac response to the pacing pulse.

* * * * *

UNITED STATES PATENT AND TRADEMARK OFFICE
CERTIFICATE OF CORRECTION

PATENT NO. : 7,720,535 B2  Page 1 of 1
APPLICATION NO. : 11/209975
DATED : May 18, 2010
INVENTOR(S) : Quan Ni et al.

It is certified that error appears in the above-identified patent and that said Letters Patent is hereby corrected as shown below:

In the Claims

Column 13, Claim 2, line 12: "farther" should be --further--.

Signed and Sealed this

Tenth Day of August, 2010

David J. Kappos
*Director of the United States Patent and Trademark Office*